United States Patent [19]
Tanihata

[11] Patent Number: 5,879,627
[45] Date of Patent: Mar. 9, 1999

[54] AUTOMATIC SAMPLE INJECTOR

[75] Inventor: Hiroshi Tanihata, Kyoto, Japan

[73] Assignee: Shimadzu Corporation, Kyoto, Japan

[21] Appl. No.: 749,196

[22] Filed: Nov. 14, 1996

[30] Foreign Application Priority Data

Jan. 30, 1996 [JP] Japan ................................ 8-037513

[51] Int. Cl.⁶ ............................ G01N 21/00; G01N 1/00; G01N 35/02
[52] U.S. Cl. ............................ 422/67; 422/100; 422/105; 422/108; 422/116; 436/50; 436/54; 436/180; 73/864.81; 73/863.81
[58] Field of Search ............................ 422/99, 100, 105, 422/89, 864.81, 864.87, 863.81, 864.16, 116, 50, 108, 70, 81; 436/50, 54, 180

[56] References Cited

U.S. PATENT DOCUMENTS 4,000,654  1/1977  Harris, Jr. ............................ 73/863.81
4,347,215  8/1982  Sisti et al. ................................ 422/63

*Primary Examiner*—Ponnathapura Achutamurthy
*Assistant Examiner*—P. Ponnaluri
*Attorney, Agent, or Firm*—Majestic, Parsons, Siebert & Hsue P.C.

[57] ABSTRACT

An automatic sample injector for a gas chromatograph includes not only a syringe with a barrel and a plunger which is adapted to move inside the barrel but also a plunger-driving motor for pushing and pulling the plunger inward and outward inside the barrel, a position sensor for the plunger and an abnormality detector for detecting an abnormal operating condition of the plunger. The plunger-driving motor has a variable torque, and it is operated at a preliminarily determined reduced torque smaller than the normal torque at which it is operated under normal conditions. The subsequent motion of the plunger, or lack thereof, is monitored by the position sensor to determine whether the plunger is totally or partially stuck inside the barrel.

8 Claims, 2 Drawing Sheets

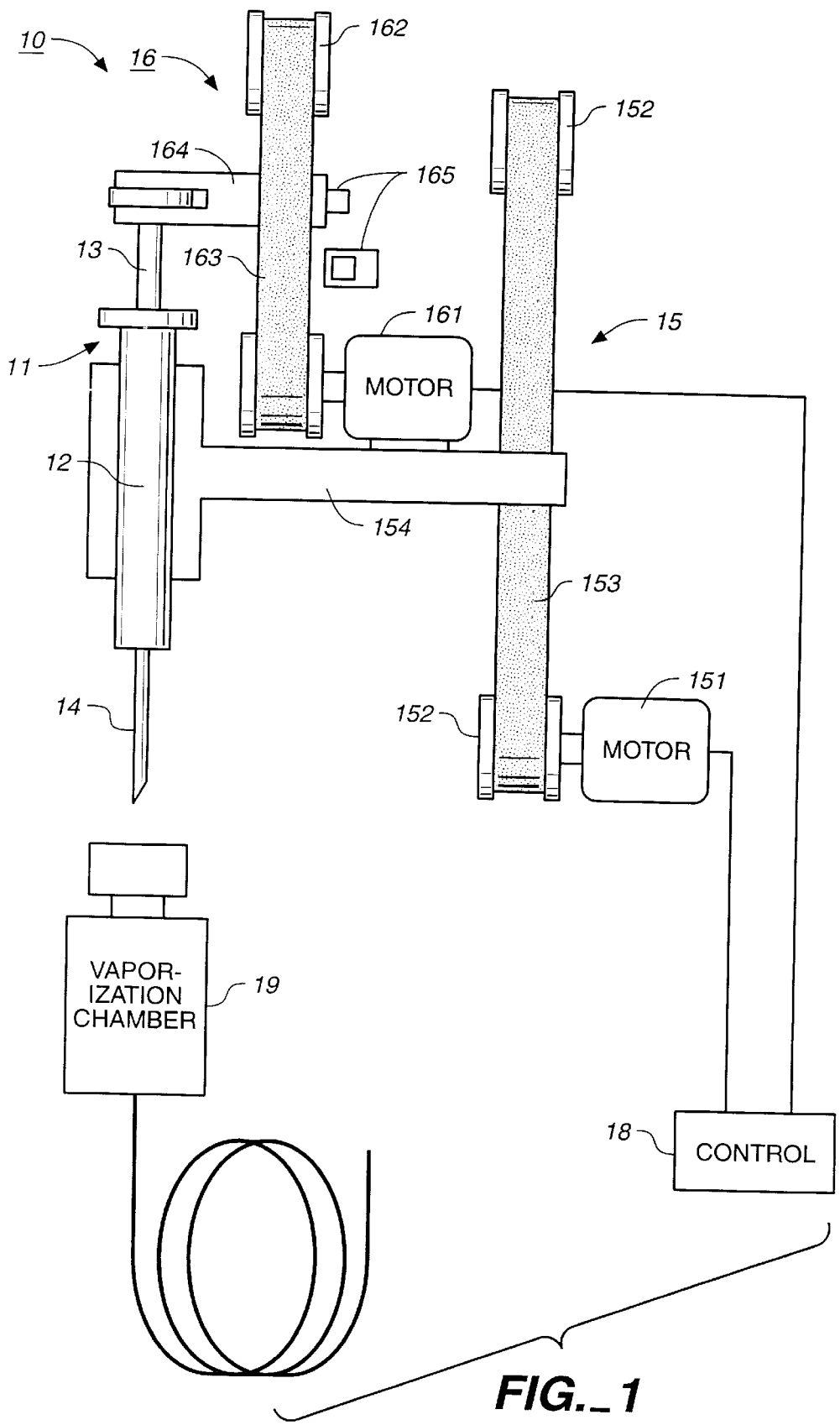
FIG._1

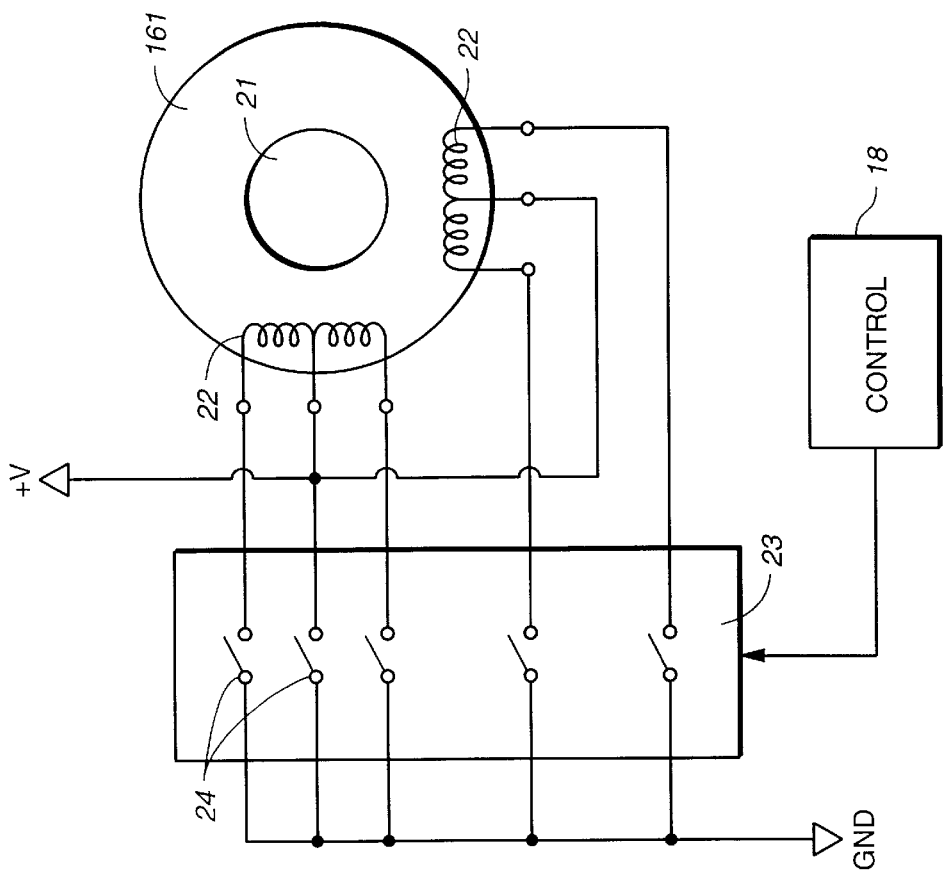
FIG._3
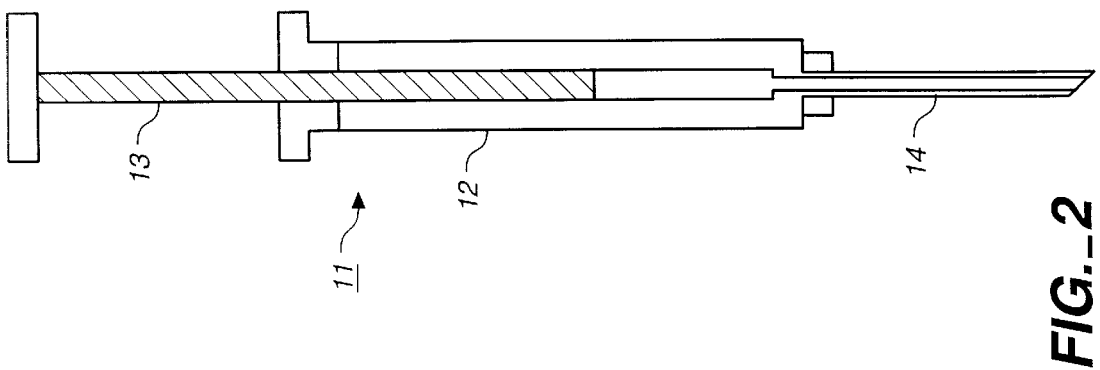
FIG._2

AUTOMATIC SAMPLE INJECTOR

BACKGROUND OF THE INVENTION

This invention relates to an automatic sample injector for injecting a liquid sample into the vaporization chamber of a gas chromatograph.

A syringe is commonly used for injecting a liquid sample to be vaporized for analysis into a gas chromatograph. Such a syringe comprises a barrel, a plunger adapted to slide inside the barrel in a liquid-tight relationship therewith, and a needle at the tip of the barrel having a liquid passage therethrough. After a liquid sample is introduced into the barrel, the needle is caused to penetrate a septum (a rubber membrane) and is inserted into the vaporization chamber such that the liquid sample can be dispersed. The liquid sample is made into particles as it is sprayed, vaporized by the heat in the vaporization chamber and transported into the chromatograph column by a carrier gas which is introduced into the vaporization chamber.

An automatic sample injector is for carrying out these processes automatically, comprising a syringe-driving mechanism for moving the syringe with respect to the vaporizer and inserting the needle into the vaporization chamber and a plunger-driving mechanism for moving the plunger with respect to the barrel so as to suck in a liquid sample into the barrel or to inject it out of the barrel. There may also be provided means for moving the syringe between a sample bottle and the vaporizer and for cleaning the barrel and the needle.

One of the problems with automatic sample injectors is that the plunger sometimes gets stuck inside the barrel and cannot be moved. A pulse motor is usually used for driving the plunger but since it is controlled in an open loop, it may appear to the motor (or the control unit therefor) as if the injector is operating normally even when the plunger is stuck inside the barrel and the injector is not operating normally at all. After a specified number of pulses is transmitted to the motor, for example, the control unit of the driving mechanism takes it for granted that the plunger has already moved and starts the next operation. If the plunger is stuck, the needle may be pulled out of the vaporization chamber before the liquid sample is completely injected thereinto, and subsequent processes will be carried out as if there was no abnormality. Since the automatic injector is used for analyzing many samples continuously, many analyses will thus be wasted in the case of such an accident. If the motor has a stronger torque than the force holding the plunger, there may be a damage to the plunger which is usually made of a metallic material such as stainless steel and is very thin (about $\phi 1$ mm×several cm).

In order to prevent such occurrences, it has been known to provide an automatic sample injector with a sensor for detecting the plunger at a specified home position (such as the position of the plunger when it is inserted most deeply) and to check whether the plunger has come back to the home position after a specified number of pulses has been transmitted from the control unit to the motor or whether the plunger has left the home position.

Although a prior art detector of this kind can detect an abnormal condition when the plunger does not return to the home position or leave the home position, this relates to a situation when the plunger is completely stuck to the barrel and cannot move at all. When the plunger is stuck but not completely and it can still move a little although the resistance is very strong, however, a prior art detector will not identify it as an abnormality, and there remains the possibility that the suction and injection of the sample may not be carried out as intended before the system moves onto the next process. If the motor has a strong torque, furthermore, the plunger is again likely to be damaged.

SUMMARY OF THE INVENTION

It is therefore an object of this invention to provide an improved automatic sample injector for a gas chromatograph capable of detecting any abnormal condition of the plunger preliminarily and thereby preventing incorrect operations of the gas chromatograph and damage to the device components.

An automatic sample injector embodying this invention, with which the above and other objects can be accomplished, may be characterized as comprising a plunger motor with variable torque for moving the plunger inside the barrel of the syringe, a plunger position sensor for detecting the plunger at a specified position, and an abnormality detecting means for detecting an abnormal condition of the plunger by first operating the plunger motor at a smaller torque than the normal torque for actual operation and by using the plunger position sensor.

The abnormality detecting means serves to drive the plunger motor at a smaller torque (referred to as "the test torque") than the torque (referred to as "the actual torque") at the time of actual operation before this automatic sample injector is actually used for the injection of a sample for real analysis. In order to preliminarily determine the magnitude of the test torque, the operator first determines a minimum torque, which is required for pushing the plunger into or out of the barrel to suck in or push out a solvent when the syringe is under normal condition. Next, the plunger is pulled fully outward from the barrel without pulling it out of the barrel and is then stopped such that it will not move. Next, the plunger is pushed in and the maximum torque at which the motor can be driven without damaging the plunger is determined, and the test torque is set somewhere between this minimum torque and the maximum torque. Since the minimum torque and the maximum torque thus defined depend on the individual injector, the test torque should be set separately for each injector.

As the injector is run at the test torque, as described above, the plunger position sensor is used to check whether the plunger is functioning correctly or not. If the plunger is somewhere other than the home position at the beginning of a test run, for example, it is determined whether the plunger comes back to the home position within a specified time determined from this initial position of the plunger. If the plunger is at the home position at the beginning, on the other hand, it may be checked whether the plunger leaves the home position within a specified period of time. In this manner, it is possible to check not only whether the plunger is completely stuck inside the barrel or not, but also whether or not an abnormally large force is being required to push in or pull out the plunger although the plunger is not completely stuck.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic structural diagram of an automatic sample injector embodying this invention;

FIG. 2 is a sectional view of the syringe of FIG. 1; and

FIG. 3 is a schematic simplified diagram for showing the structure of the stepping motor of FIG. 1 and its control unit.

DETAILED DESCRIPTION OF THE INVENTION

The invention is further described by way of an example with reference to drawings. FIG. 1 shows an automatic sample injector 10 embodying this invention for a gas chromatograph with its vaporization chamber shown at 19, comprising a syringe driving mechanism 15 for moving a syringe 11 up and down and a plunger driving mechanism 16 for moving a plunger 13 of the syringe 11 up and down. The syringe driving mechanism 15 comprises a (syringe-driving) motor 151 and a pair of pulleys 152 affixed with respect to the sample vaporization chamber 19, a belt 153 which is stretched between these pulleys 152 and a syringe clamper 154 attached to the belt 153. The plunger driving mechanism 16 comprises a (plunger-driving) motor 161 set on the syringe clamper 154, a pair of pulleys 162 affixed with respect to the syringe clamper 154, a belt 163 stretched between these pulleys 162 and a plunger clamper 164 attached to the belt 163. The plunger driving mechanism 16 further includes a home position sensor 165 comprised of light emitting and receiving units set on a side of the syringe clamper 154 and a reflective mirror affixed to the plunger clamper 164 such that the presence of the plunger 13 at its home position is detected because the light from the light emitting element is reflected by the mirror to the light receiving element when the plunger 13 is pushed into the barrel 12 of the syringe 11 as deeply as possible. FIG. 2 shows the structure of the syringe 11 more in detail. Same symbols are used both in FIGS. 1 and 2 to indicate the same components for convenience.

The plunger-driving motor 161 of the plunger driving mechanism 16 is a stepping motor having many magnetic poles 22 and ON-OFF switches 24 each associated with corresponding one of the magnetic poles 22, as shown schematically in FIG. 3. Each of the ON-OFF switches 24 comprises a FET, and the entire assembly is controlled as a FET array 23 by a control unit 18 which serves to open individual switches 24 of the array 23 for a specified period time to excite the corresponding magnetic poles of the stepping motor 161 to thereby cause its rotor 21 to rotate by a desired angle. In other words, the angle of rotation by the rotor 21 is controlled by the number of pulses outputted from the control unit 18. Each pulse for causing the rotor 21 to rotate by a specified angle comprises a large number of fine pulses such that the control unit 18 can vary the rotary torque of the stepping motor 161 by changing the duty ratio of these fine pulses.

Operations of the control unit 18 when an actual analysis is carried out by the gas chromatograph will be explained next. First, the syringe driving mechanism 15 lifts the syringe 11 to its raised position and a container (not shown) containing a sample is placed in the space between the sample vaporization chamber 19 and the needle 14 of the syringe 11. After the syringe driving mechanism 15 lowers the syringe 11 such that the needle 14 goes into the sample inside the sample container, the plunger driving mechanism 16 is activated to pull up the plunger 13 to cause a specified amount of the sample to be introduced into the barrel 12 of the syringe 11. The syringe 11 is then lifted, and after the needle 14 is taken out of the sample container, the sample container is removed from the space. The placing and removal of the sample container may be carried out by means of an auto-sampler of a known kind.

In order to inject the sample now contained inside the syringe 11 into the sample vaporization chamber 19, the syringe driving mechanism 15 causes the syringe 11 to move downward such that the needle 14 of the syringe 11 will enter the sample vaporization chamber 19 by penetrating a septum at the top thereof. The syringe driving mechanism 15 is provided with a stopper (not shown) which serves to stop the downward motion of the syringe 11 when the tip of the needle 14 reaches a specified position inside the sample vaporization chamber 19. Immediately thereafter, the plunger driving mechanism 16 pushes the plunger 13 downward until its lower end comes into contact with the bottom of the barrel 12, causing the specified amount of the sample to be sprayed inside the sample vaporization chamber 19. According to the embodiment described above, this position of the plunger 13 serves as its home position.

Prior to the actual operation for a real analysis as described above, the automatic sample injector 10 according to this invention is run as follows to check whether the plunger 13 is operable normally. First, the presence of the plunger 13 at the home position is ascertained. Thereafter, the control unit 18 controls the FET array 23 and transmits a specified number of pulses to the plunger-driving motor 161 for the same torque (duty ratio) as for the actual run. The number of pulses in this situation is set such that the plunger 13 under a normal condition will be sent to the position protruding from the barrel 12 as far out as possible without falling off therefrom. After all these pulses are transmitted, the home position sensor 165 checks whether the plunger 13 has left the home position. If the plunger 13 has not left the home position, it means that the plunger 13 is stuck at the home position, and the control unit 18 concludes that the syringe 11 is in an abnormal condition.

If the home position sensor 165 discovers that the plunger 13 is not found at the home position, the same number of pulses as above is transmitted to rotate the plunger motor 161 but at a test torque, which is smaller than the torque at the time of actual analysis. The magnitude of the test torque is preliminarily determined, as explained above, so as to be larger than the minimum torque required for the plunger 13 to move inside the barrel 12 but smaller than the torque at the time of actual analysis such that the plunger will not be bent and damaged. As explained above, the exact magnitude of the test torque should preferably be determined preliminarily for each device. With the magnitude of the test torque thus set, the plunger 13 should return to its home position after a specified number of pulses have been transmitted if the syringe 11 is in normal condition. Thus, it can be determined by checking the output of the home position sensor 165 after these pulses are transmitted whether the plunger 13 is experiencing any difficulty in moving inside the barrel 12. After the condition of the plunger 13 is thus tested successfully, the actual operation for real analysis as described above is carried out.

Although the invention was described above by way of an example wherein the plunger 13 is normally at its home position, this is not intended to limit the scope of the invention. The device may be operated such that the plunger 13 is preliminarily moved to the home position with a test torque before the testing process described above is carried out. In such a case, the number of pulses corresponding to the total stroke of the plunger may be transmitted and an abnormal condition can be detected if the plunger 13 is thereafter found not to have reached the home position.

In summary, an automatic sample injector according to this invention is adapted to carry out a test run at a low torque before it is used for a real analysis such that it is possible to detect not only the kind of abnormal condition wherein the plunger is completely stuck inside the barrel of the syringe but also situations where the plunger can be moved but the force required to do so is abnormally great. Thus, incorrect injection of sample at the time of actual analysis can be prevented and damage to the plunger can also be avoided.

What is claimed is:

1. An automatic sample injector comprising:

a syringe with a barrel and a plunger which is adapted to move inside said barrel;

a plunger-driving motor with variable torque for pushing and pulling said plunger inward and outward inside said barrel, said plunger-driving motor having associated therewith a minimum torque which is required to move said plunger inside said barrel;

a position sensor for detecting the presence of said plunger at a specified position; and an abnormality detector for detecting an abnormal operating condition of said plunger from a result of detection by said position sensor while said plunger-driving motor is being operated at a test torque which is larger than said minimum torque but is smaller than a normal torque at which said plunger-driving motor is normally operated under a normal condition.

2. A method of finding an abnormal condition in an automatic sample injector which includes a syringe with a barrel and a plunger which is adapted to move inside said barrel and a plunger-driving motor with variable torque for pushing and pulling said plunger inward and outward inside said barrel, said method comprising the steps of:

determining a test torque which is smaller than a normal torque at which said plunger-driving motor is operated under a normal condition when said automatic sample injector is used for an actual analysis;

operating said plunger-driving motor at said test torque before said automatic sample injector is used for an actual analysis; and finding that an abnormal condition exists or does not exit, depending on whether said plunger is or is not detected at a specified home position at a specified time.

3. The method of claim 2 wherein said test torque is set greater than a minimum torque which is required to move said plunger inside said barrel.

4. The method of claim 3 wherein the step of finding comprises detecting whether said plunger leaves said home position when said plunger-driving motor is operated at said test torque.

5. The method of claim 3 wherein said plunger is normally not at said home position and the step of finding comprises detecting whether said plunger is detected at said home position within a specified period of time after said plunger-driving motor is operated at said test torque.

6. The method of claim 2 further comprising the step of determining a minimum torque which is required to move said plunger inside said barrel, said test torque being set greater than said minimum torque.

7. The method of claim 6 wherein the step of finding comprises detecting whether said plunger leaves said home position when said plunger-driving motor is operated at said test torque.

8. The method of claim 6 wherein said plunger is normally not at said home position and the step of detecting presence or absence of said plunger comprises detecting whether said plunger is detected at said home position within a specified period of time after said plunger-driving motor is operated at said test torque.

* * * * *